United States Patent
Izmirli et al.

(10) Patent No.: US 11,564,769 B2
(45) Date of Patent: Jan. 31, 2023

(54) APPARATUS FOR FIDUCIAL-ASSOCIATION AS PART OF EXTRACTING PROJECTION PARAMETERS RELATIVE TO A 3D COORDINATE SYSTEM

(71) Applicant: St. Jude Medical International Holding S.à r.l., Luxembourg (LU)

(72) Inventors: Alon Izmirli, Ganot Hadar (IL); Shlomo Hoory, Gavaat-Ada (IL); Shay Levi, Kiryat Ata (IL); Itai Winkler, Nofit (IL)

(73) Assignee: ST. JUDE MEDICAL INTERNATIONAL HOLDINGS SARL, Luxembourg (LU)

( * ) Notice: Subject to any disclaimer, the term of this patent is extended or adjusted under 35 U.S.C. 154(b) by 490 days.

(21) Appl. No.: 16/393,535

(22) Filed: Apr. 24, 2019

(65) Prior Publication Data

US 2019/0328482 A1 Oct. 31, 2019

Related U.S. Application Data

(60) Provisional application No. 62/663,871, filed on Apr. 27, 2018.

(51) Int. Cl.
  *A61B 90/00* (2016.01)
  *A61B 6/00* (2006.01)
  *A61B 6/04* (2006.01)
(52) U.S. Cl.
  CPC ............ *A61B 90/39* (2016.02); *A61B 6/0407* (2013.01); *A61B 6/0492* (2013.01); *A61B 6/4441* (2013.01); *A61B 2090/3937* (2016.02); *A61B 2090/3954* (2016.02); *A61B 2090/3966* (2016.02)

(58) Field of Classification Search
  CPC ..... A61B 90/39; A61B 6/4441; A61B 6/0407; A61B 6/0492; A61B 6/12; A61B 6/487; A61B 6/503; A61B 2090/3954; A61B 2090/3966; A61B 2017/0092
  See application file for complete search history.

(56) References Cited

U.S. PATENT DOCUMENTS

| | | | |
|---|---|---|---|
| 5,299,253 A * | 3/1994 | Wessels | A61B 6/5235 378/163 |
| 7,386,339 B2 | 6/2008 | Strommer et al. | |
| 2005/0281385 A1* | 12/2005 | Johnson | A61B 34/20 378/163 |
| 2014/0114173 A1* | 4/2014 | Bar-Tal | A61B 5/0522 600/409 |

(Continued)

FOREIGN PATENT DOCUMENTS

WO 2019/155036 A3 8/2019

*Primary Examiner* — Sean D Mattson
(74) *Attorney, Agent, or Firm* — Billion & Armitage

(57) ABSTRACT

A registration fixture or plate is configured for use with a medical imaging system. The registration fixture may be an optical magnetic registration plate including a plurality of fiducial markers in arranged in a predefined unique pattern. The pattern can be unambiguously detected on 2D image of the plate produced by the medical imaging system. Association of the 2D imaged pattern of fiducial markers with the actual 3D pattern on the optical magnetic registration plate allows for accurate calculation of projection matrices and co-registration of the 3D and 2D coordinate systems.

20 Claims, 9 Drawing Sheets

(56) References Cited

U.S. PATENT DOCUMENTS

| | | | |
|---|---|---|---|
| 2015/0257846 A1* | 9/2015 | Kubiak | A61B 90/37 |
| | | | 600/407 |
| 2016/0228208 A1* | 8/2016 | Samsonov | A61B 6/0407 |
| 2016/0242724 A1* | 8/2016 | Lavallee | A61B 6/0407 |
| 2016/0267659 A1* | 9/2016 | Vasey | G06T 15/08 |
| 2017/0035382 A1* | 2/2017 | Zhang | A61B 6/547 |
| 2019/0274775 A1* | 9/2019 | Olive | A61B 34/32 |
| 2020/0046214 A1* | 2/2020 | Averbuch | G16H 30/20 |

* cited by examiner

APPARATUS FOR FIDUCIAL-ASSOCIATION AS PART OF EXTRACTING PROJECTION PARAMETERS RELATIVE TO A 3D COORDINATE SYSTEM

CROSS-REFERENCE TO RELATED APPLICATIONS

This application claims priority to U.S. provisional patent application No. 62/663,871 titled "APPARATUS FOR FIDUCIAL-ASSOCIATION AS PART OF EXTRACTING PROJECTION PARAMETERS RELATIVE TO A 3D COORDINATE SYSTEM," filed on 27 Apr. 2018, which is hereby incorporated by reference as though fully set forth herein.

BACKGROUND a. Field

The present disclosure relates to an optical-magnetic registration plate, including a predefined pattern of fiducial elements, which can be used to register 2D X-ray images within a 3D coordinate system.

b. Background

A wide variety of medical devices may be inserted into the body to diagnose and treat various medical conditions. Catheters, for example, are used to perform a variety of tasks within human bodies and other bodies, including the delivery of medicine and fluids, the removal of bodily fluids, and the transport of surgical tools and instruments. In the diagnosis and treatment of atrial fibrillation, for example, catheters may be used to deliver electrodes to the heart for electrophysiological mapping of the surface of the heart and to deliver ablative energy to the surface of the heart.

Catheters are typically routed to a region of interest through the body's vascular system. In a conventional catheterization, a micro-puncture needle (e.g., a Seldinger needle) is used to puncture the skin surface to gain access to, for example, a femoral artery, and a guide wire is then inserted through the needle before the needle is removed. A catheter sheath with a dilator inserted in it is then inserted over the guide wire. The dilator and the guide wire are then removed, leaving the sheath in place in the femoral artery. The sheath has an inner diameter greater than the outer diameter of a catheter to be used in the procedure. The catheter is then inserted into the sheath, and the sheath and/or catheter are subsequently threaded through the vasculature to a region of interest. Typically, but not necessarily, the catheter is then moved longitudinally relative to the sheath so as to extend from the distal end of the sheath to the region of interest. The longitudinal movement may be done either manually by a clinician or through the use of electromechanical drive systems.

It is desirable to track the position of medical devices such as catheters as they are moved within the body so that, for example, drugs and other forms of treatment are administered at the proper location and medical procedures can be completed more efficiently and safely. One conventional means to track the position of medical devices within the body is fluoroscopic imaging. Fluoroscopy is disadvantageous, however, because it subjects the patient and physician to undesirable levels of electromagnetic radiation. As a result, medical device navigation systems have been developed to track the position of medical devices within the body. These systems typically rely on the generation of electrical or magnetic fields and the detection of induced voltages and currents on position sensors attached to the medical device and/or external to the body. The information derived from these systems is then provided to a physician through, for example, a visual display. Oftentimes, a representation of the medical device is displayed relative to a computer model or one or more images (including, but not limited to, fluoroscopic images) of the anatomical region in which the device is being maneuvered. In order to display the medical device at the correct location relative to the model or image, the model or image must be registered within the coordinate system of the navigation system. This can be accomplished by having a set of fiducial markers that can be detected on the image or model and also be associated with known locations within the navigation system. The foregoing discussion is intended only to illustrate the present field and should not be taken as a disavowal of claim scope.

BRIEF SUMMARY OF THE DISCLOSURE

A classic technique for registration of two or more coordinate systems includes using fiducial objects ("fiducials") that are associated with known locations in each coordinate system. In cases where some or all of the fiducials cannot be distinguished individually, the present disclosure suggest that fiducial identification (i.e., fiducial association) can be performed with a pattern of fiducials (i.e., a spatial relation among the fiducials) having an unambiguous, distinct x-ray image for every possible projection (according to some partially known parameters).

The present disclosure describes an optical magnetic registration fixture (usually a plate) configured for use with a medical imaging system. The optical magnetic registration fixture includes a plurality of 3D fiducial markers in arranged in a predefined unique pattern. The pattern can be unambiguously detected on 2D image of the plate produced by the medical imaging system. Association of the 2D imaged pattern of fiducial markers with the actual 3D pattern on the optical magnetic registration fixture allows for accurate calculation of projection matrices and co-registration of the 3D and 2D coordinate systems. The above pattern must also comply with other registration technique requirements, such as allowing for an adequate degree of accuracy, relatively easy manufacturing, and minimal interference for any allowed projection.

In an embodiment, a registration fixture configured for use with a medical imaging system comprises: a first plurality of fiducial markers arranged in a first predefined pattern within the fixture; and a second plurality of fiducial markers arranged in a second predefined pattern within the fixture; wherein the first and second predefined patterns are unique such that they are distinguishably detectable, with respect to each other, on a 2D image of the fixture produced by the medical imaging system.

In another embodiment, a registration system configured for use with a medical imaging system comprises: a registration fixture including a plurality of fiducial markers arranged in a plurality of unique subsets of fiducial markers, each of the subsets being arranged in a predefined pattern within the fixture; a plurality of magnetic tracking elements; and a processor configured to calculate a plurality of projection matrices from a 3D-coordinate system of the fixture to a 2D-coordinate system of an image of the fixture produced by the medical imaging system; wherein each of the subsets is unique such that they are distinguishably detectable, with respect to one another, on the image of the fixture.

The foregoing and other aspects, features, details, utilities, and advantages of the present disclosure will be apparent from reading the following description and claims, and from reviewing the accompanying drawings.

DETAILED DESCRIPTION

Figure 1:
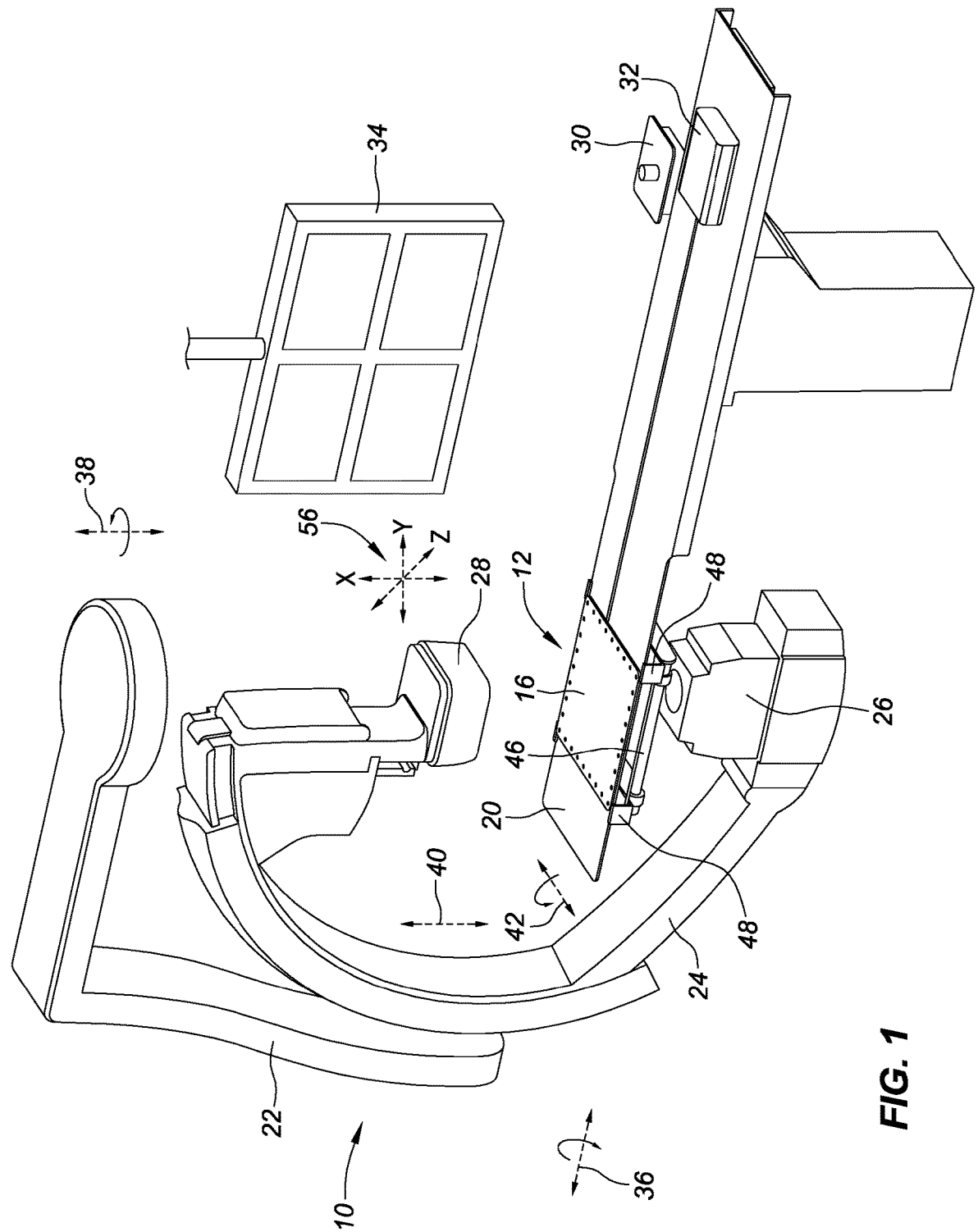
FIG. 1 is a diagrammatic view of an electrophysiology lab including an imaging system and an optical magnetic registration system, in accordance with an embodiment of the present teachings.

Referring to the drawings wherein like reference numerals are used to identify identical components in the various views, FIG. 1 illustrates an electrophysiology lab including an imaging system 10 (e.g., a fluoroscopic or other imaging system) and a registration system 12. The registration system 12 may comprise an optical-magnetic registration system for calculating the geometric relationship between the actual locations of fiducial markers 14 (see FIGS. 5-10) within an optical-magnetic registration fixture or plate (also referred to as "omni-magnetic registration plate," "omnimagnetic registration fixture," "OMRP plate," "OMRP fixture," "plate," or "fixture") 16 and the detected positions of the fiducial markers 14 within an image generated by the imaging system 10. In an embodiment, the fiducial markers 14 comprise radiopaque markers (described further below with respect to FIGS. 5-10) and the OMRP plate 16 comprises radiolucent material, such that the fiducial markers 14 are visible on a fluoroscopic image generated by the imaging system 10. In an alternative embodiment, the fiducial markers 14 may be radiolucent and the OMRP plate may be radiopaque.

Figure 2:
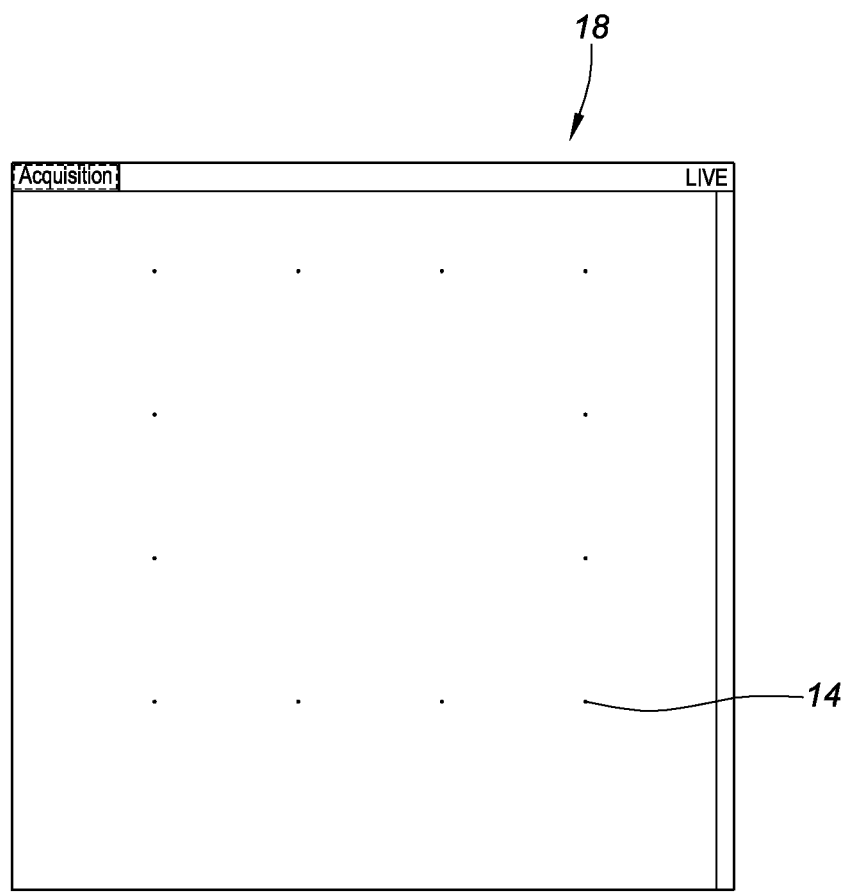
FIG. 2 is an isometric view of an example of a fluoroscopic image including individual fiducial markers.
Figure 3A:
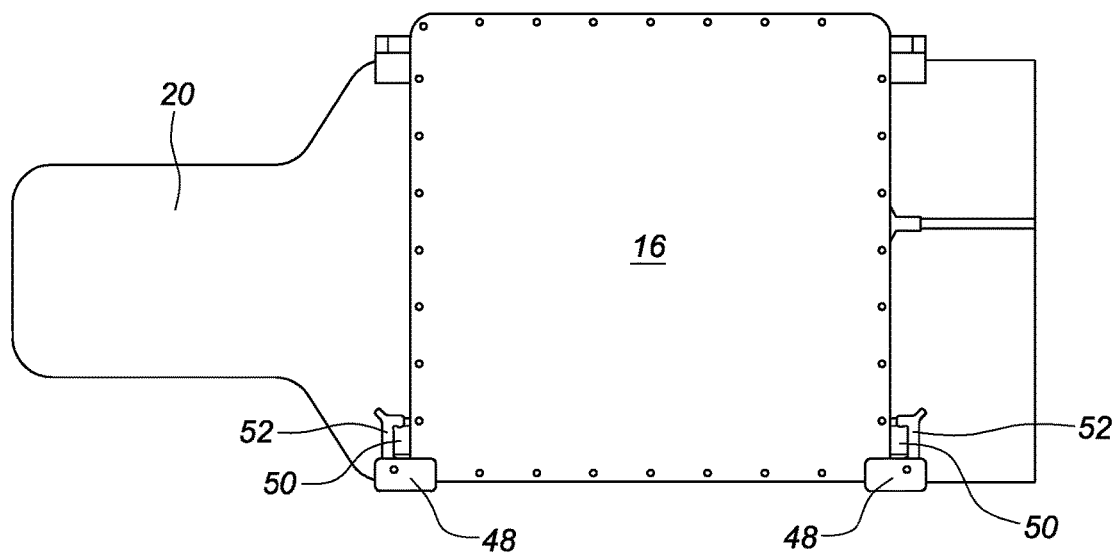
FIG. 3A is an isometric view of an example of an optical magnetic registration plate and means for attaching it to a magnetic transmitter and/or patient table.
Figure 3B:
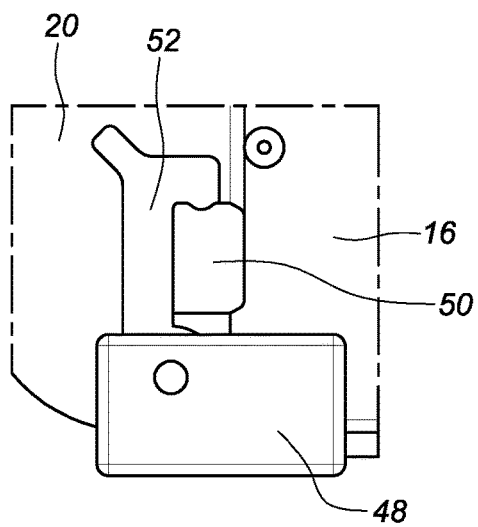
FIG. 3B is an enlarged view of section B from FIG. 3A, showing the transmitter clamp bracket in a closed configuration.
Figure 3C:
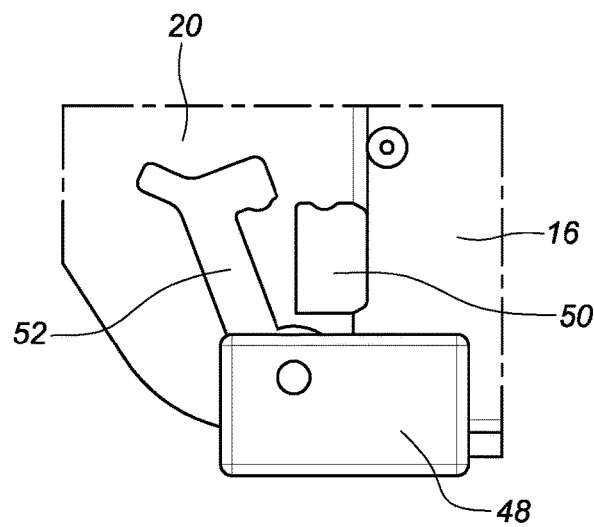
FIG. 3C is an enlarged view of section B of FIG. 3A, showing the transmitter clamp bracket in an open configuration.
Figure 4A:
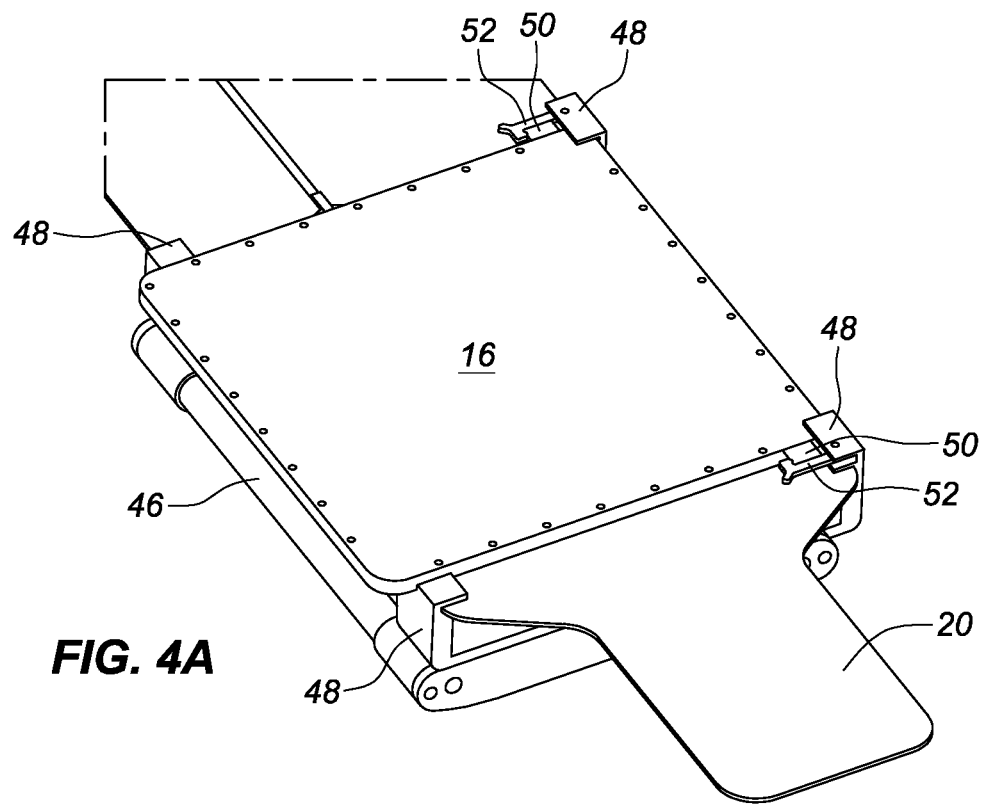
FIG. 4A is an isometric view of portions of the optical magnetic registration system.
Figure 4B:
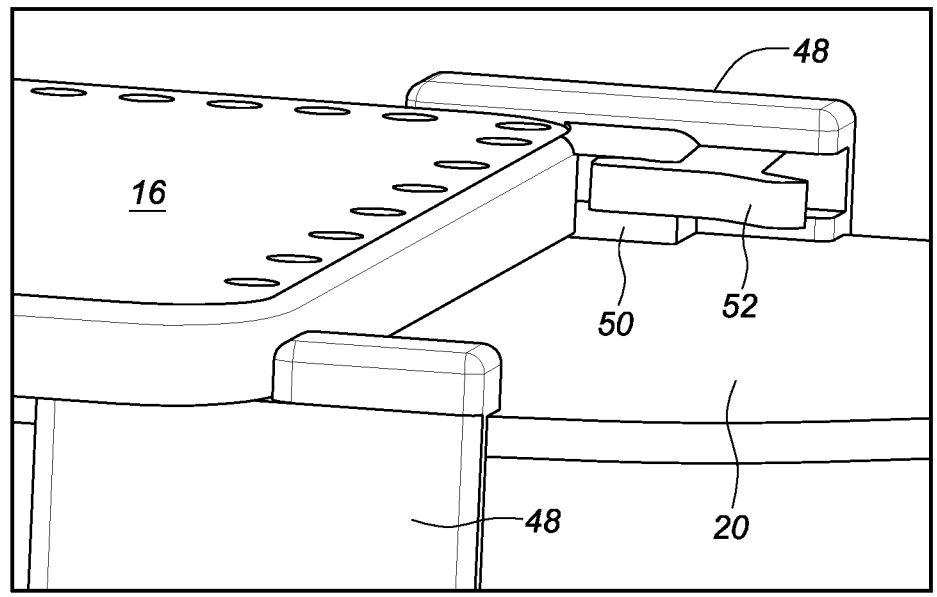
FIG. 4B is an enlarged side-angle view of section B of FIG. 4A.

When a patient's body (not shown for clarity) is positioned on a table 20 within the electrophysiology lab, a region of interest, such as the patient's heart (not shown for clarity), may overlay the OMRP plate 16, such that images of the patient's heart include images of the fiducial markers 14. For example, FIG. 2 illustrates images of fiducial markers 14 captured on a fluoroscopic image or x-ray 18, which may be displayed on a display 34 (described below with respect to FIG. 1). Complete or partial inclusion of a unique and unambiguous (e.g., distinguishably detectable) predetermined pattern of fiducial markers 14 within an image generated by the imaging system 10 allows for registration of the coordinate system of the imaging system 10 with the coordinate system of the optical-magnetic registration system 12 based on known locations of the fiducial markers 14. Registration of the two coordinate systems further allows for real-time localization of a medical device—such as an electrophysiological (EP) mapping catheter, and intracardiac echocardiography (ICE) catheter, or an ablation catheter, for example—within the patient's heart (or other region of interest) based on images including the fiducial markers 14.

The imaging system 10 is provided to acquire images of the heart or other anatomical regions of interest and comprises a fluoroscopic imaging system in the illustrated embodiment. The imaging system 10 has a structure that is movable relative to the various components of the optical-magnetic registration system 12 and relative to the patient's body and to the table 20 supporting the body. The imaging system 10 may include a number of structural components including, in the illustrated embodiment, a support 22, an arm 24, a radiation emitter 26, and a radiation detector 28. The imaging system 10 may also include an electronic control unit 30 for controlling operation of the system 10, a processing unit 32 for calculating geometry parameters of the systems 10 and 12, and output devices such as a display 34. In some embodiments, the processing unit 32 may be physically remote to the movable structure but communicatively linked thereto, such as via wired or wireless connections. The processing unit 32 can be configured to calculate geometric parameters such as, for example, projection matrices from a 3D-coordinate system of the optical-magnetic registration system 12 to a 2D-coordinate system of the imaging system. All parameters that influence the projection of a 3D-object onto a 2D-image should be taken into consideration. For example, a camera in space can have seven free parameters (three for translation, 3 for rotation, and one for focal length). The processing unit 32 can also be configured to calculate geometric parameters of the electrophysiology lab, such as, for example, source image destination, C-arm rotation, table height, table position, and digital zoom.

The support 22 provides a means for supporting and moving the arm 24, the emitter 26, and the detector 28 relative to the OMRP plate 16 (and relative to a patient's body overlaying the OMRP plate 16). Besides being connected to the arm 24, the support 22 may not be connected to other structures (as shown). In other embodiments, the support 22 may be suspended from a ceiling in the EP lab or affixed to rails (not shown) or similar structures. The support may be moved by mechanical, electrical, or electromechanical devices (not shown). The support 22 may be configured to rotate with the arm 24, the emitter 26, and the detector 28 about an axis 36 to position the arm 24, the emitter 26, and the detector 28 relative to the OMRP plate 16.

The arm 24 provides a means for supporting the emitter 26 and the detector 28 relative to the OMRP plate 16. The arm 24 may be substantially C-shaped (i.e., a "C-arm") to provide sufficient clearance relative to a patient's body and the table 20. The arm 24 is configured to rotate in either direction about an axis 38 relative to the support 22 to cause corresponding movement of the emitter 26 and the detector 28, as well as to and position the emitter 26 and the detector 28 relative to the OMRP plate 16 to permit images to be acquired from a variety of angles or orientations.

The emitter 26 is provided to emit electromagnetic radiation (e.g., x-rays) over a field of view between the emitter 26 and the detector 28, including the OMRP plate 16 and an overlying anatomical region of interest in a patient's body. The emitter 26 is disposed at one end of the arm 24. In an embodiment, the emitter 26 may be activated by a control pedal (not shown) operated by a physician, for example.

The detector 28 captures electromagnetic radiation passing through the OMRP plate 16 and anatomical region of interest in a patient's body and generates signals used to create images of the OMRP plate 16 and the region of interest. In one embodiment, the detector 28 may comprise a flat detector and may be configured to rotate about the axis 36 relative to the arm 24. The detector 28 may also be movable relative to the arm 24 along an axis 40 to vary the distance between the emitter 26 and the detector 28 (i.e., the "source to image distance" or "SID"). The detector 28 is disposed at an opposite end of the arm 24 relative to the emitter 26.

The relative movement of the imaging system 10 and other objects within the electrophysiology lab create various degrees of freedom that the optical-magnetic registration system 12 may need to account for. The arm 24 rotates about axes 36, 38, and 42, and moves along axis 40. The table 20 may move relative to the imaging system 10 (or vice versa) in either direction along three orthogonal axes resulting in as many as seven degrees of freedom.

The display 34 is provided to convey information to a physician to assist in diagnosis and treatment. The display 34 may comprise one or more computer monitors or other display devices. The display 34 may present fluoroscopy images and a graphical user interface (GUI) to the physician. The GUI may communicate a variety of information including, for example, a fluoroscopic image of an anatomical region of interest, such as a heart, along with any fiducial markers 14 on the OMRP plate 16 underlying the anatomical region of interest. Image data to the display 34 may be captured and processed by the processing unit 32, such that a 3D matrix of the fiducial markers is accurately projected onto the 2D fluoroscopic image seen on the display 34. The GUI may also communicate information regarding the anatomy of a patient's heart, electrophysiology data associated with the heart, as well as images and positional information for one or more therapeutic or diagnostic medical devices being used in or around the patient's heart.

In accordance with one embodiment of the present teachings, the optical-magnetic registration system 12 is used for associating fiducial markers 14 detected on a fluoroscopic image to their "real-world" positions on the OMRP plate 16. The optical-magnetic registration system 12 may also be used to determine the position of the imaging system 10 within coordinate system 44 and, in particular, various components of imaging system 10. The system 12 employs magnetic fields and may comprise the system made available under the trademark MediGuide™ by St. Jude Medical, Inc. and generally shown and described in, for example, commonly owned U.S. Pat. No. 7,386,339, the entire disclosure of which is incorporated herein by reference.

The system 12 may include magnetic field transmitters 46, which can be associated with (e.g., releasably fixed to) the OMRP plate 16 or located within the OMRP plate 16. In the embodiment shown in FIG. 1, the magnetic field transmitters 46 are positioned at fixed locations with respect to the OMRP plate 16 via transmitter clamps 48, which may clamp onto the OMRP plate 16 via grooves (not shown) in the OMRP plate 16 and/or another means of attachment. As shown in FIGS. 3A-3C and 4A-4B, the OMRP plate 16 may include tabs or extensions 50 that protrude outward from the OMRP plate 16 at or near one or more of its four corners. Transmitter clamp brackets 52 can close around the extensions 50 to more securely hold the OMRP plate 16 in place with respect to the transmitters 46.

Magnetic field transmitters 46 generate magnetic fields that cause a response in magnetic sensors indicative of the location and orientation of the magnetic sensors within the magnetic fields and within coordinate system 56. In an embodiment, magnetic tracking elements such as the magnetic field transmitters 46 and/or magnetic field sensors may be located within the OMRP plate 16. In another embodiment, the magnetic sensors may be located at the periphery of the OMRP plate 16 so as to limit potential interference with the X-ray field of view. Additional magnetic field sensors (not shown) may be located within a medical device, on a patient, or at other locations within coordinate system 56.

Figure 5:
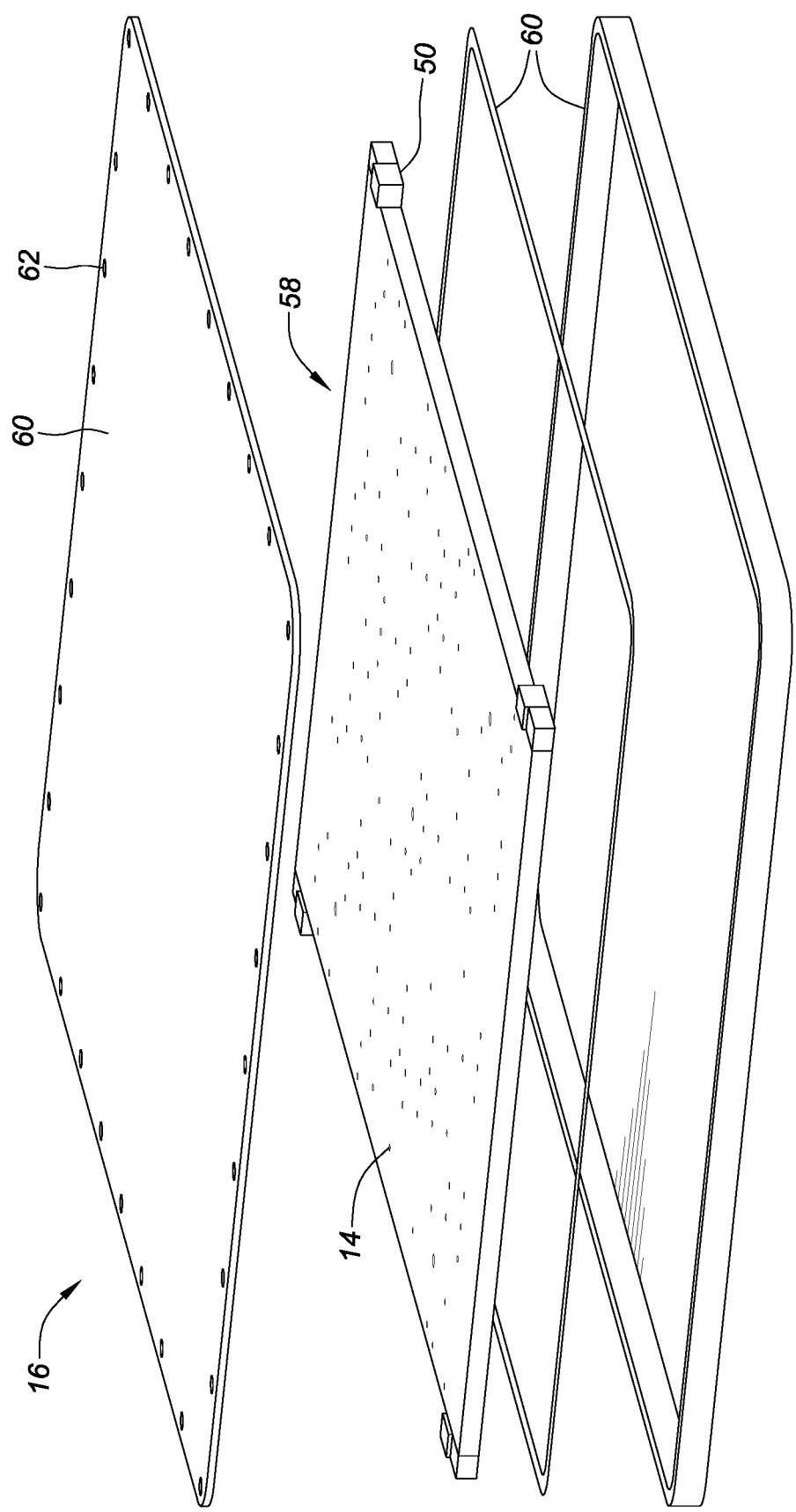
FIG. 5 is an exploded view of an example of an optical magnetic registration plate.

Turning now to FIG. 5, further details of the OMRP plate 16 are shown and described. The OMRP plate 16 may be comprised of a rigid internal structure 58 including fiducial markers 14 arranged in a pattern. As described above with respect to FIGS. 3A-3C and 3A-3B, tabs or extensions 50 may protrude at or near one or more of the four corners of the internal structure 58 of the OMRP plate 16. These extensions 50 may be used to secure the internal structure 58 in place within a protective housing 60 and/or with respect to other elements, such as the table 20 or the transmitters 46 (shown in FIGS. 1 and 4A). Screws or rivet heads 62 may be used to attach the housing 60 to the internal structure 58 of the OMRP plate 16. Further details regarding the protective housing 60 and/or the OMRP plate 16 and/or associated components may be found in commonly owned U.S. Patent Application No. 62/629,086, the entire disclosure of which is incorporated herein by reference.

Turning now to FIGS. 6-9, additional details are shown and described regarding the fiducial markers 14 and their unique patterns, as well as the resulting ability to associate images of the fiducial markers 14 captured by the imaging system 10 with their actual positions on the OMRP plate 16. The fiducial markers 14 used in the OMRP plate 16 may be 3D markers, such as small, identical, radio-opaque balls. (In other embodiments, the radiopaque elements can comprise balls of more than one size and/or lines and/or any other shape that can be visualized under x-ray imaging.) In an embodiment, the radio-opaque balls can be made of steel or tungsten. Using a plurality of identical fiducial markers 14 provides several implementation advantages, such as manufacturing simplicity. In addition, when the three-dimensional fiducial markers 14 are projected onto an image (e.g., a fluoroscopic image produced via imaging system 10), the projection of the identical balls is similar from every angle.

Since each of the fiducial makers 14 are identical, size cannot be used to differentiate among them. Instead, unique predefined patterns of the fiducial markers 14, in conjunction with prior and sufficiently accurate knowledge of the parameters of imaging system 10, can be used to associate each visible image of a fiducial marker 14 with its corresponding physical fiducial marker 14 in the OMRP plate 16. Specifically, the fiducial markers 14 can be organized in a pattern (i.e., a spatial relation among the fiducial markers 14) that yields a distinct x-ray image for every possible projection. In order to organize the fiducial markers 14 in a sufficiently unique, unambiguous pattern, the present inventors developed patterns with a minimal number of fiducials in each possible image. A minimal density pattern is required to facilitate accurate calculation of projection matrices from the 3D OMRP plate 16 onto the 2D fluoroscopic image obtained via imaging system 10 (i.e., registration of the 3D coordinate system with the 2D coordinate system). A minimal density pattern also provides the advantages of easier image processing and manufacturing. In addition, a minimal density pattern provides minimal interference with, or minimal obstruction of, the anatomical region being imaged.

A patterned OMRP plate can have dimensions such that, for a large range of possible imaging system parameters (e.g., source image destination, C-arm rotation, table height, table position, digital zoom, and other mechanical considerations), at least a portion of the patterned plate is located in the path of the x-ray beam. Thus, the portion of the plate that is captured on the x-ray image may vary. In addition, the shape of the observed pattern of fiducial markers may vary or be distorted according to the imaging system parameters. Accurate detection of the unambiguous patterns must remain despite these variances and distortions. In general, the patterned fiducial markers 14 should be distant enough from each other to prevent elements from overlapping under large C-arm angles. One possible approach for defining a pattern includes generating many random or pseudo-random patterns, and choosing the best one according to the above criteria.

Figure 6:
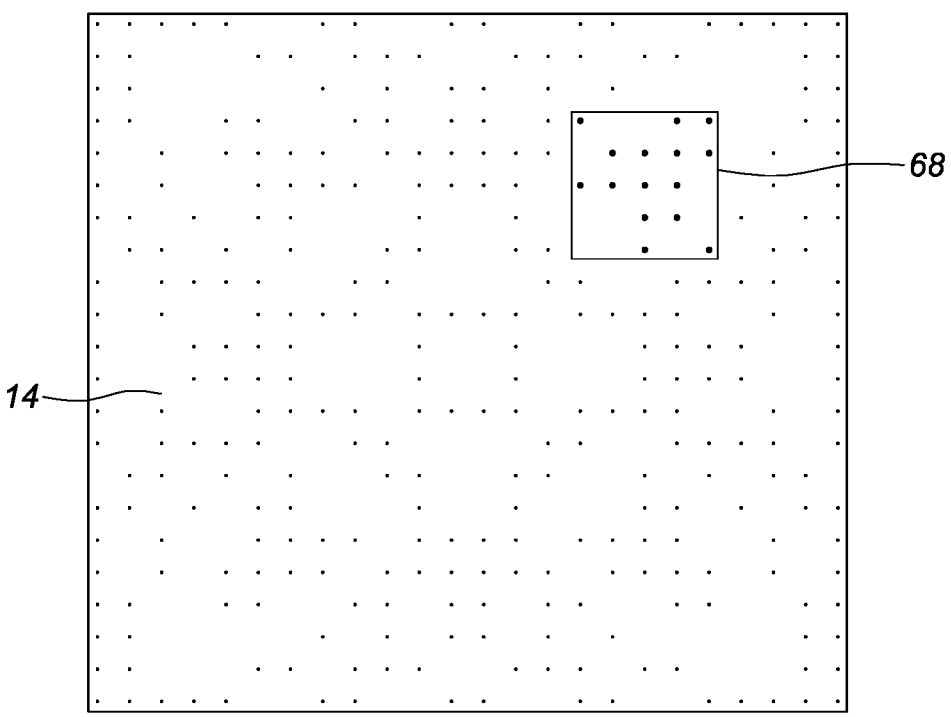
FIGS. 6-10 are diagrammatic views of examples of various unique patterns of fiducial markers that may be included within an optical magnetic registration plate.

FIG. 6 illustrates an embodiment of a unique pattern of fiducial markers 14 for use in an OMRP plate 16. The pattern can be further divided into sub-patterns or sub-windows, such as 5×5 sub-window 68. In an embodiment, each possible 5×5 sub-window can include a unique pattern of fiducial markers 14. In another embodiment, each possible 5×5 sub-window can include a unique pattern of fiducial markers 14 even if one or more of the individual fiducial markers 14 is undetected, incorrectly detected, or falsely detected (e.g., detection of non-existing fiducials). For example, assume that, within a given 5×5 window, three radiopaque fiducial elements captured on an x-ray image are not detected in the OMRP plate. In this case, the uniqueness of each 5×5 sub-window would still be maintained. Likewise, if three fiducial markers within a given 5×5 sub-window of the patterned OMRP plate are not properly captured on the x-ray image, the uniqueness of each 5×5 sub-window would still be maintained.

Figure 7:
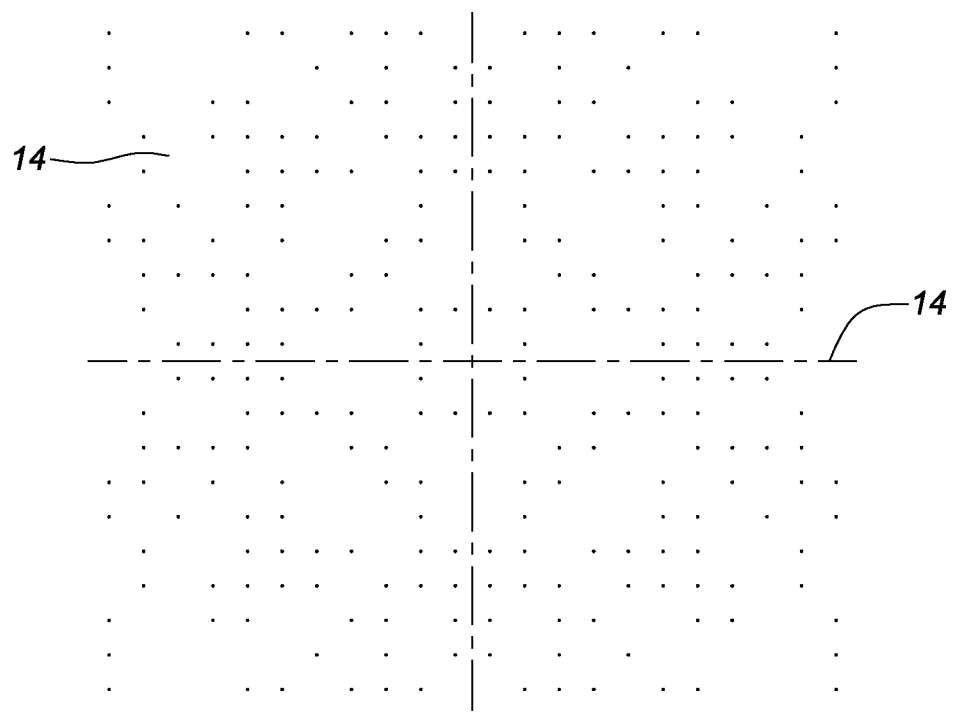

In addition to using unique sub-patterns as shown in FIG. 6, there are other ways to produce unique patterns of fiducial elements 14 on an OMRP plate 16. For example, symmetric rectangular grids in which each grid fiducial element may be present or excluded, are shown in FIG. 7. Other symmetric grids, such as squares, hexagons, or circles, may also be used. In another embodiment, random or pseudo-random dispersion of fiducial elements can be used within the grid. FIG. 7 also illustrates an example of a wedged pattern in which each of four identical wedges have rotational symmetry. It should be noted that the fiducial elements 14 in FIG. 7 include both radiopaque balls and line elements.

Figure 8:
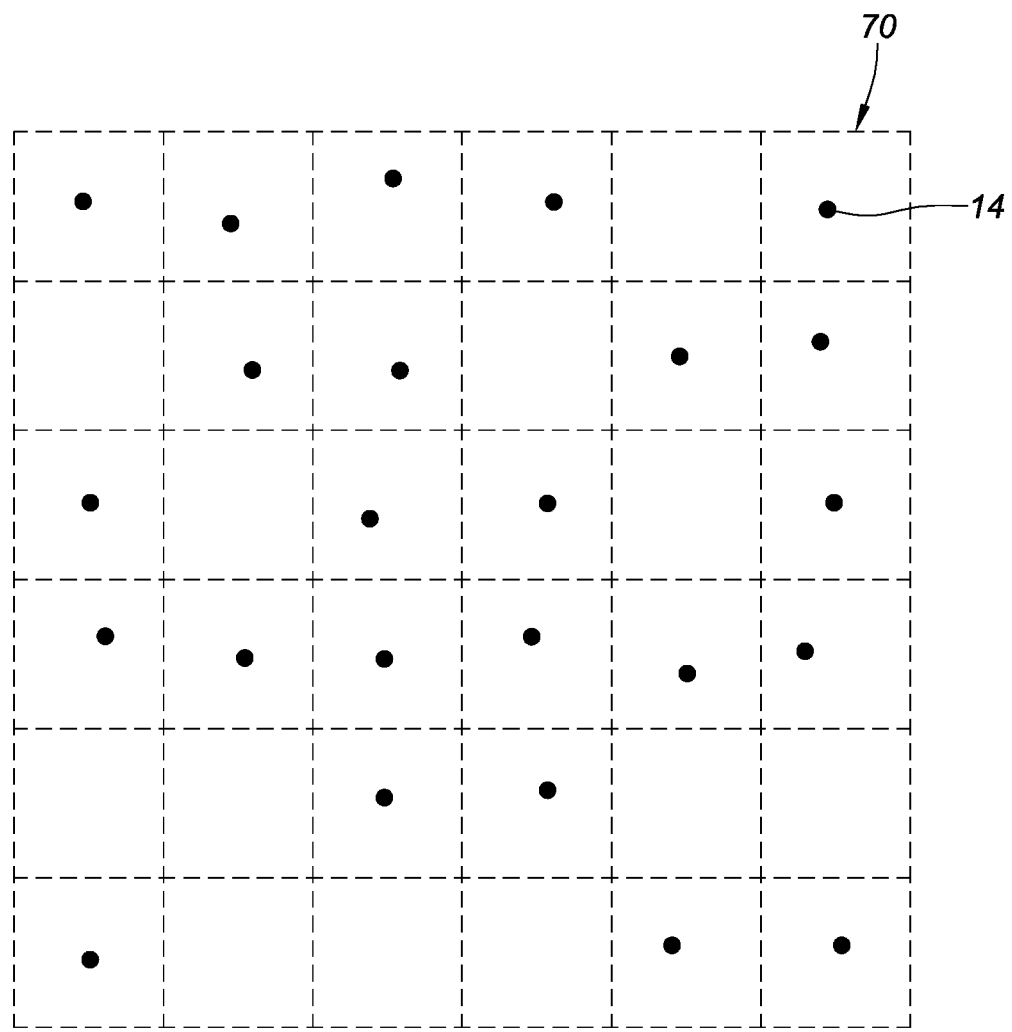

FIG. 8 illustrates another embodiment of a unique pattern of fiducial markers 14 in an OMRP plate that involves the use of tiles 70. Zero, one, or more fiducial markers 14 can be designated to occupy the center of each tile. When the 3D pattern of fiducial markers 14 is projected onto a 2D image, the exact location of the tile borders may be unknown. Nevertheless, if the potential offset of each fiducial marker 14 from the center of its respective tile is limited, the pattern can still be recognized (despite ambiguity of tile border locations). In an example (not shown), two or more types of tiles can be used. For instance, there may be multiple tile types, where each type of tile has a different type of fiducial marker. Additionally, tile types can be differentiated based on the number of fiducial markers present in each tile. Finally, tile types can be differentiated based on unique sub-patterns of fiducial markers within each tile type.

Figure 9A:
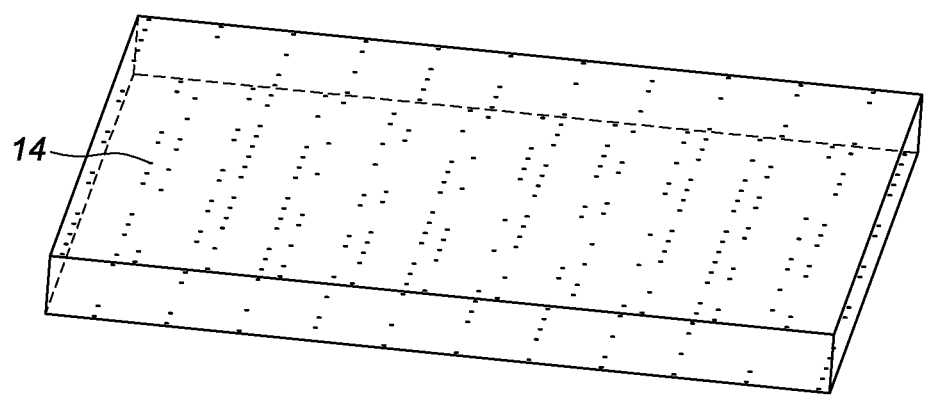
Figure 9B:
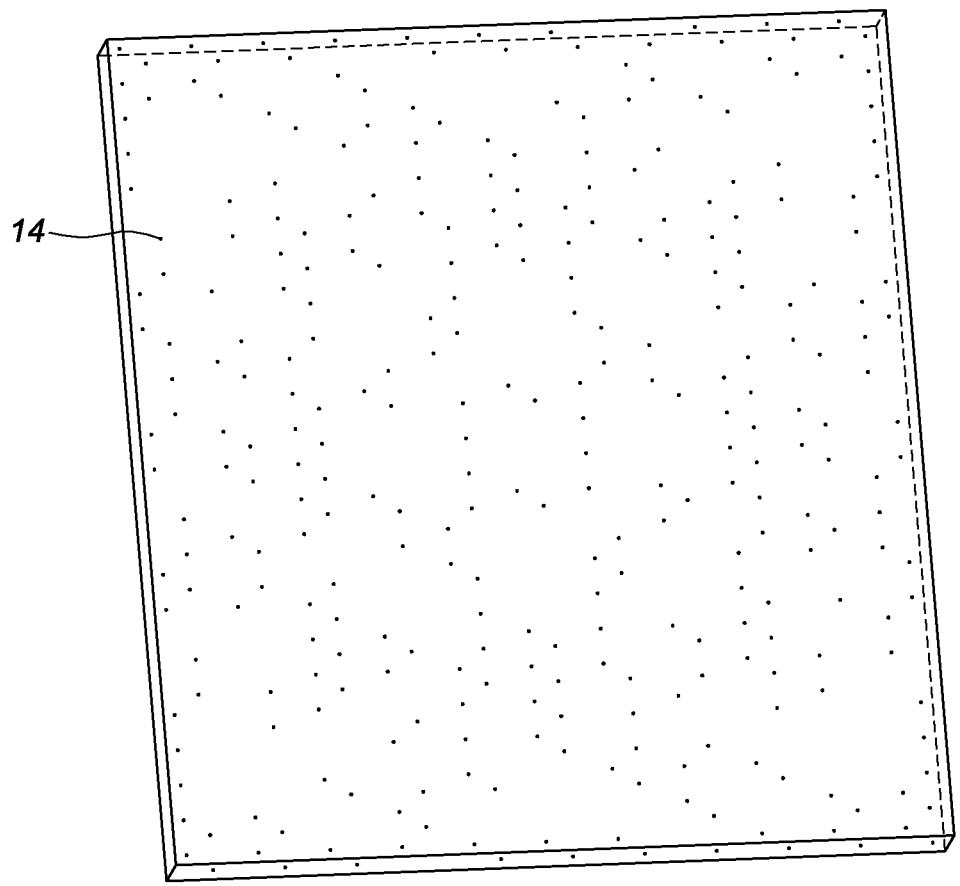

FIGS. 9A and 9B illustrate another embodiment of a pattern of fiducial markers 14 including a multi-layered pattern. Multi-layered patterns in which fiducial markers are distributed in the volume of an OMRP plate (rather than in a single plane) can also provide the required uniqueness for accurate and unambiguous coordinate system registration.

Figure 10:
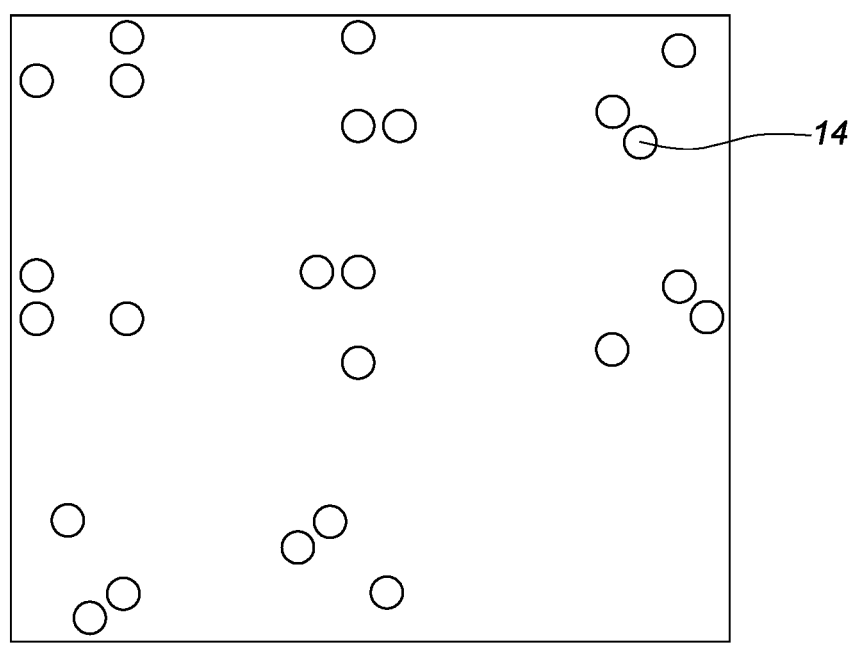

Yet another embodiment of includes a coded pattern comprising a set of sub-patterns, as shown in FIG. 10. Each sub-pattern can be viewed as a letter, digit, or symbol; thus, the entire plate can be viewed as a sequence of rows and columns of symbols. In the example shown in FIG. 10, each sub-pattern is comprised of three ball-shaped fiducials, and each sub-pattern is flipped or rotated at a specified angle. The ordering of the sub-patterns generates a larger coded pattern and allows for maintenance of the uniqueness (assuming at least one sub-pattern is visible) that is required for association of the imaged sub-patterns with their positions within the larger plate.

Although several embodiments have been described above with a certain degree of particularity, those skilled in the art could make numerous alterations to the disclosed embodiments without departing from the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed:

1. A registration fixture configured for use with a medical imaging system, the registration fixture comprising:
   a first plurality of fiducial markers arranged in a first predefined pattern within the fixture;
   a second plurality of fiducial markers arranged in a second predefined pattern within the fixture; and
   a plurality of magnetic transmitters coupled to the registration fixture,
   wherein the first and second predefined patterns are unique such that they are distinguishably detectable, with respect to each other, on a two-dimensional (2D) image of the fixture produced by the medical imaging system, wherein the registration fixture is configured to fixedly couple to a patient table to secure the registration fixture under a patient throughout a procedure, wherein the first and second pluralities of fiducial markers define a three-dimensional (3D) coordinate system, wherein the 2D image defines a 2D coordinate system, and wherein the 3D coordinate system and the 2D coordinate system are co-registered by associating a first position of at least one of the first or second pluralities of fiducial markers detected on the 2D image with a second position of the at least one of the first or second pluralities of fiducial markers within the fixture, wherein the first or second predefined patterns comprise a plurality of sub-patterns, and wherein each of the plurality of sub-patterns comprises a unique and unambiguous arrangement of fiducial markers such that each of the plurality of sub-patterns is distinctly identifiable, with respect to each other, on the 2D image, wherein each of the plurality of sub-patterns comprises a symmetric grid, and wherein the first and second predefined patterns are configured to allow the medical imaging system to determine a majority of possible projections from the medical imaging system.

2. The fixture of claim 1, wherein the medical imaging system is an x-ray imaging system, and wherein the first and second pluralities of fiducial markers are radiolucent or radiopaque.

3. The fixture of claim 2, wherein the x-ray imaging system includes a c-arm.

4. The fixture of claim 2, wherein at least a portion of the fixture is located within a path of an x-ray beam.

5. The fixture of claim 1, wherein the first and second pluralities of fiducial markers comprise balls or line elements.

6. The fixture of claim 5, wherein the first and second pluralities of fiducial markers comprise identically-sized metal balls.

7. The fixture of claim 1, wherein the first and second predefined patterns of fiducial markers are configured to allow viewing of a majority of a field of view of the medical imaging system.

8. The fixture of claim 1, wherein the fixture is fixed with respect to at least one of the plurality of magnetic field transmitters.

9. The fixture of claim 1, wherein at least one magnetic tracking element is embedded within the fixture.

10. The fixture of claim 1, wherein the medical imaging system includes the patient table, and wherein the fixture is configured to be placed on top of the patient table.

11. The fixture of claim 1, wherein at least one of the first and second predefined patterns are multi-layered, such that at least one of the first or second plurality of fiducial markers are dispersed in a plurality of layers within the fixture.

12. The fixture of claim 1, wherein the first or second predefined patterns are distinguishably detectable on the 2D image.

13. A registration system configured for use with a medical imaging system, the registration system comprising:
   a registration fixture including a plurality of fiducial markers arranged in a plurality of unique subsets of fiducial markers, each of the subsets being arranged in a predefined pattern within the fixture;
   a plurality of magnetic tracking elements;
   a plurality of magnetic transmitters coupled to the registration fixture; and
   a processor configured to calculate a plurality of projection matrices from a three-dimensional (3D) coordinate system of the fixture to a two-dimensional (2D) coordinate system of an image of the fixture produced by the medical imaging system;
   wherein each of the subsets is unique such that they are distinguishably detectable, with respect to one another, on the image of the fixture, wherein the registration fixture is configured to fixedly couple to a patient table to secure the registration fixture under a patient throughout a procedure, wherein a first subset and a second subset of the plurality of unique subsets define the three-dimensional (3D) coordinate system, wherein the image defines the 2D coordinate system, wherein each of the subsets comprises a symmetric grid, and wherein the plurality of fiducial markers are configured to allow the medical imaging system to determine a majority of possible projections from the medical imaging system.

14. The system of claim 13, and wherein the processor is configured to associate each subset of the subsets of fiducial markers detected on the image with the corresponding subset of fiducial markers in the fixture.

15. The system of claim 13, wherein the plurality of fiducial markers comprise radiopaque balls or line elements.

16. The system of claim 13, wherein the plurality of magnetic tracking elements comprises magnetic sensors.

17. The system of claim 16, wherein at least one magnetic sensor of the magnetic sensors is embedded within the fixture.

18. The system of claim 13, wherein at least some of the fiducial markers cannot be distinguished individually.

19. The system of claim 13, wherein the predefined pattern of each of the subsets is unambiguously detectable on the image.

20. The system of claim 13, wherein each and every of the plurality of subsets is unique such that they are distinguishably detectable with respect to one another, on the image of the fixture.

* * * * *